United States Patent [19]

Kashima

[11] Patent Number: 5,142,462
[45] Date of Patent: Aug. 25, 1992

[54] ILLUMINATING OPTICAL SYSTEM

[75] Inventor: Shingo Kashima, Hachiouji, Japan

[73] Assignee: Olympus Optical Co., Ltd., Tokyo, Japan

[21] Appl. No.: 515,617

[22] Filed: Apr. 27, 1990

[30] Foreign Application Priority Data

Apr. 28, 1989 [JP] Japan .................. 1-111291

[51] Int. Cl.⁵ ................................ F21V 5/00
[52] U.S. Cl. .................. 362/268; 362/259; 362/331; 356/318; 359/642
[58] Field of Search ............... 362/259, 268, 331, 223; 350/448, 449, 409; 356/73, 318, 71; 359/642, 738, 739

[56] References Cited

U.S. PATENT DOCUMENTS

| | | | |
|---|---|---|---|
| 3,710,933 | 1/1973 | Fulwyler et al. | 209/3 |
| 3,981,562 | 9/1976 | Anthon | 356/71 X |
| 4,350,892 | 9/1982 | Kay et al. | 250/461.2 |
| 4,690,561 | 9/1987 | Ito | 356/73 X |
| 4,715,708 | 12/1987 | Ito | 356/73 X |

Primary Examiner—Stephen F. Husar
Attorney, Agent, or Firm—Cushman, Darby & Cushman

[57] ABSTRACT

The illuminating optical system comprises a light source for emitting a light beam having an elongated sectional shape in parallel with the optical axis thereof, and a condenser lens for focusing said light beam onto a sample. This illuminating optical system permits easily correcting aberrations in the lens system thereof, assures little loss of light amount, has high operability and can easily be manufactured.

3 Claims, 4 Drawing Sheets

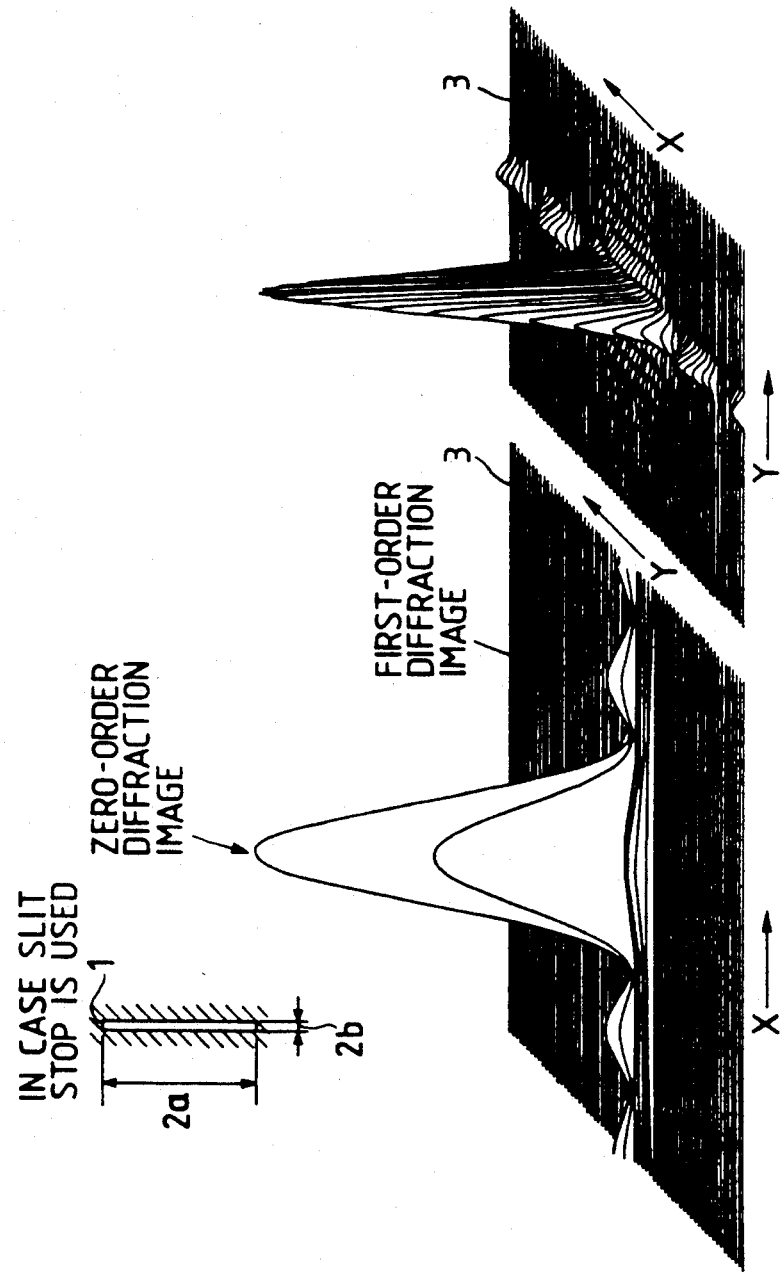

NAa >> NAb

INCIDENT CIRCULAR COLLIMATED BEAM

EXIT SLIT-LIKE COLLIMATED BEAM

ILLUMINATING OPTICAL SYSTEM

BACKGROUND OF THE INVENTION

1. Field of the Invention

The present invention relates to an illuminating optical system which is adapted to be capable of illuminating samples or the like with a thin slit-like beam.

2. Description of the Prior Art

The conventional illuminating optical systems of this type are mainly classified into three types which are adapted:

(1) to prepare a slit-like beam by passing a collimated light through a slit and allowing the slit-like beam to fall directly onto a sample without transmitting said slit-like beam through an objective lens, (2) to form a contracted image of a slit by irradiating a slit with a light emitted from a light source and allowing the image of the slit to fall onto a sample, and (3) to form a fringe pattern in the vicinity of a sample by allowing two laser beams to interfere with each other and allow a portion having the highest light intensity of the fringe pattern to fall onto the sample through a slit placed immediately before the sample.

However, the optical system of the type (1) requires, for obtaining a thin slit-like beam, a very thin slit which is difficult to manufacture and increases loss of light amount in practice. Further, the optical system of the type (2) poses a problem that the operability deteriorates remarkably since the distance between the objective lens and the sample (working distance) shortens if the objective lens is intended to have high contraction ratio. Furthermore, when the optical system of the type (2) uses two objective lenses at the same time, these objective lenses will interfere with each other. Accordingly, the optical system of the type (2) prevents use of objective lenses having so high contraction ratios, and requires, for obtaining a slit-like beam, a thin slit not so extreme as the thin slit for the optical system of the type (1), and poses the problem similar to that of the optical system of the type (1). Moreover, when an optical member functioning as a cylindrical lens (for example, a thin water flow) exists between the objective lens and the sample as in a case of light measurement using a flow cytometer (hereinafter abbreviated as F.C.M.), the optical system of the type (2) poses a problem that the optical member functioning as a cylindrical lens has a longitudinal refractive index which is different from the lateral refractive index thereof, and the optical system cannot form an image of the slit having favorably corrected aberrations only with the objective lens which is a coaxial system. Moreover, the optical system of the type (3) poses a problem that, when it uses diffracted beams, the fringe pattern is blurred unless the pattern is formed on the sample and the slit must be placed almost in contact with the sample, thereby remarkably degrading the optical system. In addition, the optical system of the type (3) uses only the central portion the fringe pattern and causes remarkable loss in the amount of light.

SUMMARY OF THE INVENTION

In view of the problems described above, it is a primary object of the present invention to provide an illuminating optical system which permits easy correction of aberrations in the lens system thereof, assures little loss of light amount, has high operability and can be manufactured easily.

The illuminating optical system according to the present invention is equipped with a light source means for emitting a light beam having an elongated sectional shape parallel to the optical axis of the illuminating optical system, and a condenser lens for focusing said light beam onto a sample, whereby said illuminating optical system is adapted to permit efficiently using a collimated light beam and prevent an image from being formed on the sample surface.

The illuminating optical system according to the present invention has a pupil in the shape of a slit therefore, the shape of a diffraction image scarcely deforms due to aberrations and defocusing in the direction perpendicular to the slit if aberrations in the longitudinal direction of the slit are corrected.

This and other objects as well as the features and advantages of the present invention will become apparent from the following detailed description of the preferred embodiments when taken in conjunction with the accompanying drawings.

BRIEF DESCRIPTION OF THE DRAWING

FIG. 2 and FIG. 3 are diagrams illustrating shapes of stops and paraxial diffraction images corresponding to the shapes of the stops respectively;

DETAILED DESCRIPTION THE PREFERRED EMBODIMENTS

Now, the present invention will be described in detail with reference to the preferred embodiments illustrated in the accompanying drawings.

Figure 1:
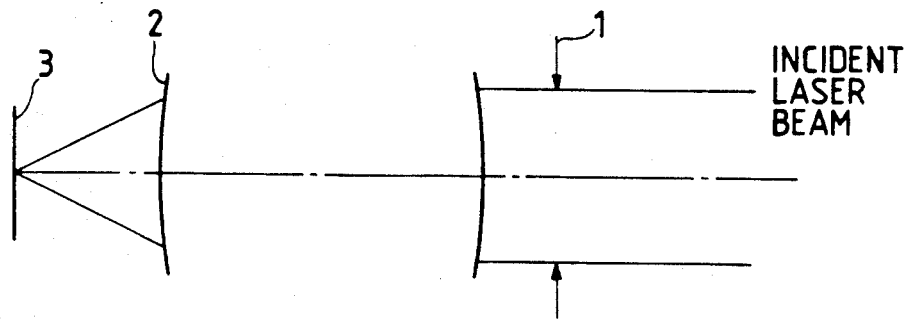
FIG. 1 is a schematic diagram illustrating Embodiment 1 of the illuminating optical system according to the present invention.
Figure 2:
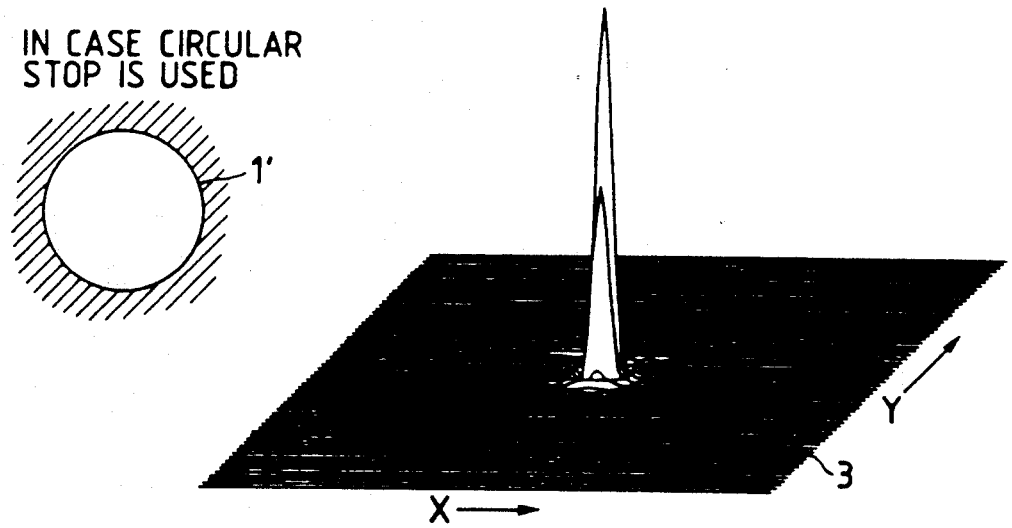

FIG. 1 shows the Embodiment 1 wherein a slit-like collimated light is formed by passing an incident laser beam (a collimated light) through a slit stop 1 and a slit-like beam is formed at the focal point of an objective lens by allowing other collimated light to be incident on the objective lens (condenser lens) 2. The slit-like beam means here a beam having a rectangular, elliptic or other sectional shape which has a longitudinal length at least twice as long as the lateral length thereof. When the collimated light having passed through a circular stop 1 is focused onto a sample surface 3 by the objective lens 2 which is aplanatic, the paraxial diffraction image becomes an image, shape obtained by Fourier transformation, of the shape (usually circle) of the pupil of the objective lens 2 (See FIG. 2). In Embodiment 1 of the present invention wherein the collimated beam having passed through the slit stop 1 is allowed to be incident on the objective lens 2, in contrast, the entire optical system including the objective lens 2 has a pupil in the shape of the slit and the paraxial diffraction image has a slit-like shape which is obtained by Fourier transformation of the shape of the slit (See FIG. 3).

A rectangular slit stop will be taken as a typical example for the following description.

Let us assume that the objective lens 2 has a focal length of f, and the slit-like collimated beam has a sectional area of $2a \times 2b$ and a wavelength of $\lambda$. When x-y coordinates are set on the sample surface 3 (focal point), intensity distribution I (x, y) of the diffraction image on the sample surface 3 is:

$$I(x, y) = [(\sin aX)/aX]^2 \cdot [(\sin bY)/bY]^2$$

wherein $X \equiv (2\pi/\lambda f)x$, and $Y \equiv (2\pi/\lambda f)y$

Since intensity of the first-order diffraction image is several percents at highest of the intensity of the zero-order diffraction image and more than 80% of light amount exits in the zero-order diffraction image, it may be considered that the diffraction images consist only of the zero-order diffraction image (See FIG. 3). Since values of x and y which first give I (x, y)=0 (these values will be represented as $x_0$ and $y_0$ respectively) are calculated as follows:

$$x_0 = (\lambda/2) \cdot (f/a) \text{ and } y_0 = (\lambda/2) \cdot (f/b)$$

size of the zero-order diffraction image, i.e., size of the beam is expressed by the formula:

$$2x_0 \cdot 2y_0 = (\lambda f/a) \cdot (\lambda f/b)$$

Hence, it is possible to obtain a slit-like beam having an optional shape by varying a and b.

Figure 4A:
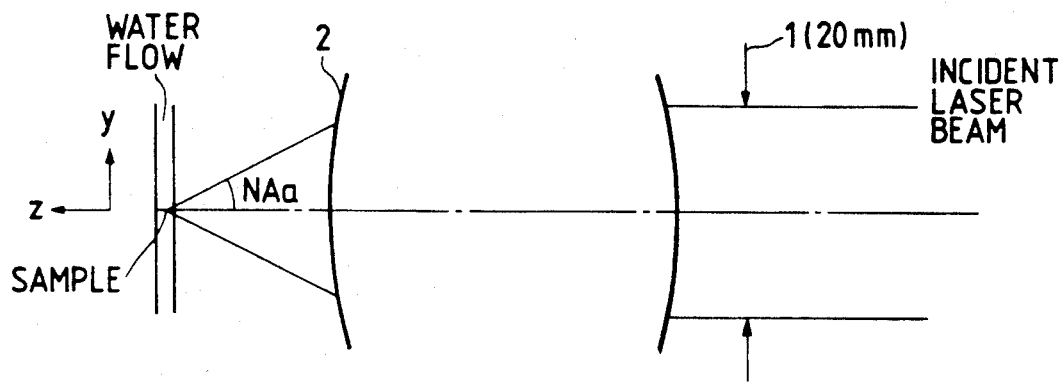
FIG. 4A and FIG. 4B are a side view and a plan view respectively in a case wherein a water flow is interposed between the sample and the objective lens in the Embodiment 1 of the present invention.
Figure 4B:
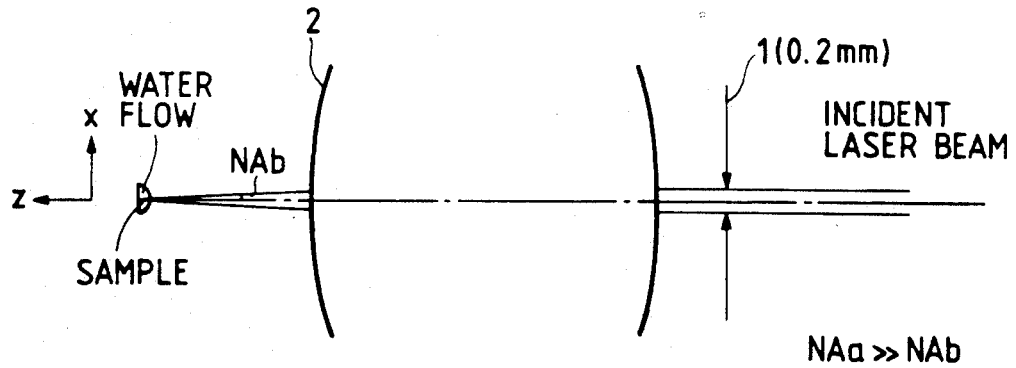

Next, F.C.M. will be described below as an example. In the conventional optical system of the type (2) which is designed for projecting a contracted image of a slit, since the water flow for passing objects to be observed functions as a cylindrical lens, it is impossible to correct aberrations in both the x and y directions when the contracting lens is a coaxial system (revolutionary symmetrical system), and it is generally very difficult to correct the aberrations even by using cylindrical lenses. In contrast, since such a slit-like beam as described above can be obtained in the Embodiment 1, it is sufficient for the Embodiment 1 of the present invention to correct only the paraxial aberrations unlike the conventional optical system of the type (2). Further, since F.C.M. usually requires a very thin beam along with a very thin slit stop, the optical system is extremely different in numerical aperture (hereinafter NA) between the x direction and the y direction on the sample side, whereby the smaller NA becomes very narrow. Accordingly, quality degradation of the diffraction image due to aberrations and defocusing in the entire optical system including the cylindrical water flow and the objective lens is nearly negligible in the direction in which NA is the smaller. It is therefore sufficient for the Embodiment 1 of the present invention to correct aberrations of the objective lens only in the direction in which NA is smaller (See FIG. 4A and FIG. 4B).

As is understood from the foregoing description, Embodiment 1 of the present invention which is composed to illuminate a sample with a collimated slit-like beam while condensing it by the objective lens, does not require using a fine slit-like that of the conventional optical system of the type (1), can assure little loss of light amount and can be manufactured easily. Further, unlike the conventional optical systems of the type (2) which forms a contracted image of a slit, the Embodiment 1 of the present invention makes it sufficient to correct aberrations only in the longitudinal direction of the slit-like beam even when an optical member functioning as a cylindrical lens exits between the objective lens and the sample, and poses no problem of space since the Embodiment 1 does not require bringing the objective lens close to the sample for obtaining a minute image. Furthermore, the Embodiment 1 of the present invention assures little loss of light amount, does not require placing a slit in the vicinity of the sample and has high operability since a major part of light is included in the zero-order ray and intensities of the first and higher order rays are negligibly low.

Figure 5A:
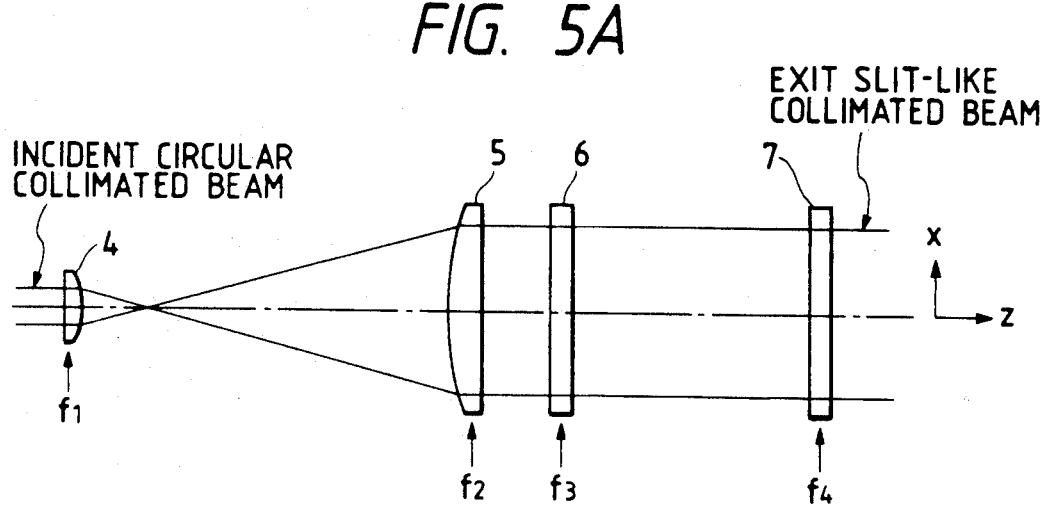
FIG. 5A and FIG. 5B are a side view and a plan view respectively of an illuminating optical system for obtaining the slit-like collimated beam in an optical system preferred as Embodiment 2 of the present invention.
Figure 5B:
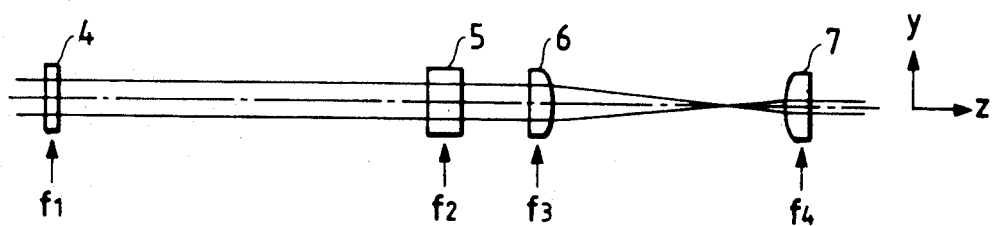

In addition to the method for obtaining the slit-like collimated light in the illuminating optical system according to the present invention by placing a slit stop in the ordinary circular collimated beam as in the Embodiment 1 described above, there is available another method for obtaining a slit-like collimated beam by varying longitudinal-to-lateral ratio of a sectional shape of a circular collimated beam with a combination of cylindrical lenses as in the Embodiment 2 of the present invention described below. FIG. 5A and FIG. 5B show a light source means used in the Embodiment 2 wherein rays emitted from an ordinary light source are collimated into a circular beam which has a diameter of D. The reference symbols $f_1$ and $f_2$ represent the focal lengths of cylindrical lenses 4 and 5 respectively which have refractive powers in the x direction, and the reference symbols $f_3$ and $f_4$ designate the focal lengths of cylindrical lenses 6 and 7 respectively which have refractive powers in the y direction. When these four cylindrical lenses 4, 5, 6 and 7 are arranged in this order in such a manner that the rear focal point of the lens 4 is coincident with the front focal point of the lens 5 and the rear focal point of the lens 6 is coincident with the front focal point of the lens 7, a beam having passed through the lens system composed of the four lenses has a sectional shape which is expressed as follows:

$$(D \times f_2/f_1) \cdot (D \times f_4/f_3)$$

It is therefore possible to obtain a slit-like beam having an optional sectional shape by adequately selecting $f_1$, $f_2$, $f_3$ and $f_4$.

In addition, it is desirable to combine the Embodiments described above when effective use of light amount and sharpness of the diffraction image are taken into consideration.

Now, examples of numerical data will be described below.

NUMERICAL DATA EXAMPLE 1

Let us consider an illuminating optical system for condensing a laser having a wavelength f of 0.5 μm into slit-like beam having a size of 1 μm × 100 μm. When the objective lens has a focal length f of 20 mm, the beam has a size expressed as follows:

$$(\lambda f/a) \cdot (\lambda f/b)$$

Since $\lambda f/a = 0.001$ and $\lambda f/b = 0.1$, we obtain a=10 mm and b=0.1 mm. That is to say, a slit-like beam having the size of 1 μm × 100 μm can be obtained by using a slit stop measuring 20 mm × 0.2 mm. Further, in a case where the collimated circular beam has a diameter D of 2 mm, and the cylindrical lenses have focal lengths $f_1$ of 10 mm, $f_2$ of 100 mm, $f_3$ of 50 mm and $f_4$ of 5 mm respectively, the exit slit-like collimated beam has a size of 20 mm ×0.2 mm which is calculated as follows:

$$(D \times f_2 f_1) \cdot (D \times f_4/f_3)$$

This illuminating optical system therefore forms the slit-like beam measuring 20 mm ×0.2 mm.

Sizes of beams generally required for the F.C.M.'s are on the order of (0.5 to 2 μm)·(50 to 200 μm. When the focal length in the longitudinal direction is represented by $f_a$ and the focal length in the lateral 0 direction is designated by $f_b$, the above-mentioned beam sizes correspond, at a wavelength of 0.5 μm, to $f_a/a$ and $f_b/b$ within the ranges defined below respectively:

$$1 < f_a/a < 4 \text{ and } 100 < f_b/b < 400$$

Further, numerical aperture $NA_a$ in the longitudinal direction and numerical aperture $NA_b$ in the lateral direction to be selected on the sample side are:

$$1 > NA_a > 0.25$$

$$0.01 > NA_b > 0.0025$$

It is therefore understood that the NA in the x direction is largely different the NA in the y direction and that the smaller NA (i.e., $NA_b$ is very narrow,

NUMERICAL DATA EXAMPLE 2

Let us assume a case wherein a sample is placed in a water flow having a diameter of 80 μm and to be measured with the F.C.M. Let us further assume that a slit-like beam having a size of 1 μm ×80 μm is to be formed at the center of the water flow by using a laser having a wavelength of 0.5 μm. Since the water flow functions as a cylindrical lens, the entire optical system including an objective lens has focal lengths which are different between the x direction and the y direction. When $f_a$ is 20 mm and $f_b$ is 16 mm, the slit-like beam has a size calculated as follows:

$$(\lambda f_a/a) \cdot (\lambda f_b/b)$$

From $\lambda f_a/a = 0.001$ and $\lambda f_b/b = 0.08$, we obtain a=10 mm and b=0.1 mm. That is to say, the illuminating optical system forms a slit-like beam measuring approximately 1 μm by 80 μm when a slit stop of 20 mm ×0.2 mm is used.

It is possible, needless to say, to form a beam having an elongated sectional shape and parallel with the optical axis by using prisms and/or similar optical members which have contracting ratios different between the longitudinal and lateral directions. Further, it is needless to say that an optical member which is to be interposed between the condenser lens and the sample, and has refractive powers different between two direction perpendicular to each other is not limited to the water flow only.

A diffraction image is generally deformed when aberrations and defocusing are remarkable. For example, when an object (for example water) which has refractive powers different between the longitudinal direction of the sectional shape of the slit-like beam and the direction perpendicular thereto is placed between the objective lens 2 and the focal point thereof, aberrations can hardly be corrected and a diffraction image is largely different from the image formed through Fourier transformation by an aplanatic system. In contrast, an illuminating optical system having a slit-like pupil such as the optical system according to the present invention is more advantageous since the optical system scarcely deforms a diffraction image due to aberrations and defocusing in the direction perpendicular to the longitudinal direction of the slit-like pupil and makes it sufficient to correct aberrations only in the longitudinal direction of the slit-like pupil.

What is claimed is:

1. An illuminating optical system comprising:
   light source means for emitting a light beam having an elongated sectional shape on a common optical axis; and
   a condenser lens for focusing said light beam onto a sample to form a diffraction image having an elongated sectional shape.

2. An illuminating optical system according to claim 1 wherein a member having refractive power different between a predetermined direction within a plane perpendicular to said optical axis and a direction perpendicular to said predetermined direction within said plane is interposed between said condenser lens and said sample.

3. An illuminating optical system according to claim 1 or 2 wherein a sectional shape of said light beam has a longitudinal length at least twice a lateral length thereof.

* * * * *